US006728663B2

(12) United States Patent
Krukar et al.

(10) Patent No.: US 6,728,663 B2
(45) Date of Patent: Apr. 27, 2004

(54) STRUCTURE IDENTIFICATION USING SCATTERING SIGNATURES

(75) Inventors: Richard H. Krukar, Albquerque, NM (US); Christopher J. Raymond, Albuquerque, NM (US); Scott R. Wilson, Corrales, NM (US); Steve W. Farrer, Albuquerque, NM (US)

(73) Assignee: Accent Optical Technologies, Inc., Bend, OR (US)

( * ) Notice: Subject to any disclaimer, the term of this patent is extended or adjusted under 35 U.S.C. 154(b) by 166 days.

(21) Appl. No.: 09/952,546

(22) Filed: Sep. 12, 2001

(65) Prior Publication Data

US 2002/0046008 A1 Apr. 18, 2002

Related U.S. Application Data

(60) Provisional application No. 60/232,578, filed on Sep. 13, 2000.

(51) Int. Cl.[7] .................................................. G06F 7/02
(52) U.S. Cl. ...................... 702/189; 702/32; 702/179; 702/188
(58) Field of Search ....................... 702/22, 27, 28–32, 702/179, 188, 189; 356/700; 89/11.1; 244/62; 376/319; 382/100

(56) References Cited

U.S. PATENT DOCUMENTS

| 5,114,233 | A | | 5/1992 | Clark et al. ................. 356/354 |
|---|---|---|---|---|
| 5,241,369 | A | | 8/1993 | McNeil et al. .............. 356/445 |
| 5,465,308 | A | * | 11/1995 | Hutcheson et al. .......... 382/159 |
| 5,682,466 | A | | 10/1997 | Maeda et al. ................. 395/50 |
| 5,703,692 | A | | 12/1997 | McNeil et al. .............. 356/445 |
| 5,739,909 | A | | 4/1998 | Blayo et al. ................ 356/369 |
| 5,867,276 | A | | 2/1999 | McNeil et al. .............. 356/445 |
| 6,075,594 | A | | 6/2000 | Thomas et al. ............. 356/328 |
| 6,122,403 | A | * | 9/2000 | Roads ........................ 382/233 |
| 6,480,299 | B1 | * | 11/2002 | Drakopoulos et al. ....... 358/1.9 |
| 6,539,095 | B1 | * | 3/2003 | Roads ....................... 381/73.1 |
| 2001/0051856 | A1 | | 12/2001 | Niu et al. ..................... 702/57 |
| 2002/0038196 | A1 | | 3/2002 | Johnson et al. ............. 702/179 |

OTHER PUBLICATIONS

Davidson, M.P. et al., "An Inverse Scattering Approach to SEM Line Width Measurements", *Proc. SPIE*, Mar., 1999, pp. 640–649, vol. 3677, Conference On Meterology, Inspection and Process Control for Microlithography XIII, Santa Clara, California.

Krukar, R.H., "A Methodology for the Use of Diffracted Scatter Analysis to Measure Critical Dimensions of Periodic Structures", Engineering Ph.D. Dissertation, May, 1993, University of New Mexico, Albuquerque, New Mexico.

* cited by examiner

*Primary Examiner*—Marc S. Hoff
*Assistant Examiner*—Felix Suarez
(74) *Attorney, Agent, or Firm*—Stephen A. Slusher

(57) ABSTRACT

A method of pruning a reference library of signatures and corresponding known structure parameter vectors, each signature composed of a reference signal vector, including, for a given reference signal vector, interpolating a parameter vector and deleting the given reference signal vector and the corresponding parameter vector for a sufficiently small interpolation error. Also a method of accessing an indexed reference library of signatures and corresponding known structure parameter vectors, each signature comprising a reference signal vector, including acquiring an unknown signal, calculating an index vector for the unknown signal; determining error between the index vector for the unknown signal and a calculated reference signal index vector of the library; and thereby identifying as a match candidate for the unknown signal a reference signal vector.

26 Claims, No Drawings

STRUCTURE IDENTIFICATION USING SCATTERING SIGNATURES

CROSS-REFERENCE TO RELATED APPLICATIONS

This application claims the benefit of the filing of U.S. Provisional Patent Application Ser. No. 60/232,578, entitled "Speed Improvements for Identifying Structures Using Scattering Signatures and a Library of Scatter Signatures from Known Structures", filed on Sep. 13, 2000, and the specification thereof is incorporated herein by reference.

BACKGROUND OF THE INVENTION

1. Field of the Invention (Technical Field)

The present invention relates to the measurement and optionally control of features in a structure, and in particular to measurement by means of inference techniques.

2. Background Art

Metrology instruments, such as scatterometers, spectral reflectometers, ellipsometers, and electron microscopes, are used to measure micron and submicron scale structures. Scatterometers, reflectometers, and ellipsometers infer the structure from a signal obtained while measuring a sample. Most electron microscopes directly image the measured signal onto a display, but recent results have shown that more accurate results may be obtained by inferring the structure in a manner similar to that used by the other techniques. M. P. Davidson, et al., "An Inverse Scattering Approach to SEM Line Width Measurements", *Proc. SPIE*, Vol. 3677, Conference on Metrology, Inspection, and Process Control for Microlithography XIII, pp. 640–645 (March 1999).

Inference via linear estimation is feasible, see, e.g., U.S. Pat. No. 5,114,233, entitled "Method for Inspecting Etched Workpieces", to Clark, et al.; R. H. Krukar, "A Methodology for the Use of Diffracted Scatter Analysis to Measure the Critical Dimensions of Periodic Structures", Engineering Ph.D. Dissertation, University of New Mexico (1993); and U.S. Pat. No. 5,739,909, entitled "Measurement and Control of Linewidths in Periodic Structures Using Spectroscopic Ellipsometry", to Blayo, et al., but generally does not yield the quality of results desired of a production metrology tool. Inference via table lookup has demonstrated production quality results, but can require more time per measurement than is available to meet throughput specifications.

The requirements on the inference techniques will become more stringent in the future. Linear estimators will require more degrees of freedom over larger data sets and lookup tables will require larger tables. In either case, there is a loss in measurement quality or an increase in time per measurement. The present invention provides a pruning and interpolation technique that greatly enhances speed of lookups.

SUMMARY OF THE INVENTION (DISCLOSURE OF THE INVENTION)

The present invention is of a system for and method of pruning a reference library of signatures and corresponding known structure parameter vectors, each signature comprising a reference signal vector, comprising: for a given reference signal vector, interpolating a parameter vector assuming that the given reference signal vector and its corresponding parameter vector were deleted from the reference library; and deleting the given reference signal vector and the corresponding parameter vector if an interpolation error between the corresponding parameter vector and the interpolated parameter vector is less than a threshold value. In the preferred embodiment, the interpolating and deleting steps are repeated a predetermined plurality of times for a plurality of given reference signal vectors. Performance of the steps is preferably submitted to a remote computer on a computer network, with results of the steps being retrieved from or returned by the remote computer. The steps are preferably performed utilizing a dedicated CD-ROM and/or ramdisk on the remote computer. Performance of the steps may be submitted and results retrieved either automatically or manually.

The present invention is also of a system for and method of accessing an indexed reference library of signatures and corresponding known structure parameter vectors, each signature comprising a reference signal vector, with the library additionally comprising a plurality of reference signal index vectors, comprising: calculating an index vector for an unknown signal; determining error between the index vector for the unknown signal and a reference signal index vector of the library; and identifying as a match candidate for the unknown signal a reference signal vector corresponding to the reference signal index vector if the error is below a predetermined threshold. In the preferred embodiment, a plurality of computer systems are employed for performing the calculating, determining, and identifying steps, wherein each of the computer systems performs the steps on a discrete portion of the reference library. Preferably calculating, determining, and identifying is performed for a plurality of reference signal index vectors. Performance of the steps is preferably submitted to a remote computer on a computer network, with results of the steps being retrieved from or returned by the remote computer. The steps are preferably performed utilizing a dedicated CD-ROM and/or ramdisk on the remote computer. Performance of the steps may be submitted and results retrieved either automatically or manually.

The invention is additionally of a system for and method of accessing an indexed reference library of signatures and corresponding known structure parameter vectors, each signature comprising a reference signal vector, with the library additionally comprising a plurality of reference signal index vectors, comprising: calculating an index vector for an unknown signal; determining an absolute difference vector from the index vector for the unknown signal and a reference signal index vector of the library; and identifying as a match candidate for the unknown signal a reference signal vector corresponding to the reference signal index vector if all values in the absolute difference vector are below corresponding values in a predetermined threshold vector. In the preferred embodiment, a plurality of computer systems are employed for performing the calculating, determining, and identifying steps, wherein each of the computer systems performs the steps on a discrete portion of the reference library. Preferably calculating, determining, and identifying is performed for a plurality of reference signal index vectors. Performance of the steps is preferably submitted to a remote computer on a computer network, with results of the steps being retrieved from or returned by the remote computer. The steps are preferably performed utilizing a dedicated CD-ROM and/or ramdisk on the remote computer. Performance of the steps may be submitted and results retrieved either automatically or manually.

Objects, advantages and novel features, and further scope of applicability of the present invention will be set forth in part in the detailed description to follow, and in part will become apparent to those skilled in the art upon examination

DESCRIPTION OF THE PREFERRED EMBODIMENTS

BEST MODES FOR CARRYING OUT THE INVENTION

The present invention is of an improved method and system for matching a measured scattering signal to a reference signal in a library. A library of reference signals is generated either through modeling and simulation or is generated empirically. The library is then pruned by removing signals that may be accurately represented via interpolation from other signals in the reference set. An index of the pruned library is then generated by correlating each signature with one or more indexing functions and then ordering the index based on the magnitude of the correlation. Finally, the index and library are loaded onto a computer, preferably a special purpose match computer. Matching is performed by submitting an unknown signal to the match computer, which correlates the unknown signal with the indexing function or functions to identify one or more signals that appear similar to the unknown signal. As appropriate, interpolation values are calculated between the unknown signal and the closest matching reference signals. The structure that resulted in the unknown structure is then calculated from the interpolation values. Details of the structure are then returned to the requester and/or are forwarded to a factory automation system, or the like.

The present invention is predicated on the fact that the time required to find the best match of an unknown signal from a large library of reference signals is dependent on over-all library size, the number of comparisons that must be performed, the time required to load the library into the computer's memory, and whether or not the library remains resident in the computer's memory.

The vectors referred to in the following description of the invention may have only one element. In the case of vectors having only one element, they are scalars and should be treated as such.

A reference signal, r, is a vector $(r_1 \ r_2 \ \ldots \ r_j)$ of measurement values obtained from a metrology tool or may alternatively be a vector of simulated measurement values obtained from a computational model. Every reference signal is associated with p, a parameter vector $(p_1 \ p_2 \ \ldots \ p_k)$, indicative of a structure which, when measured, would result in the reference signal.

An unknown signal u, is a vector $(u_1 \ u_2 \ \ldots \ u_i)$ analogous to r. The difference is that the associated parameter vector, p, is not known.

A reference library is a set of reference signals and their associated parameters.

The error $\epsilon(a,b)$ is a scalar value indicative of the difference between two vectors. Error functions employable by the invention include the mean square error, the root mean square error, absolute error, and Mahalanobis distance. If the vectors a and b are of different length, then either or both vectors may be resampled in order to yield vectors of equivalent length. A preferred resampling method is linear interpolation. Another method is frequency based resampling based on Discrete Fourier Transforms (DFT). Basis sets other than sines and cosines of the DFT can also be used. The error can be calculated in the transform space. An example of a transform space is the frequency domain representation associated with the DFT.

The match error is the error obtained when one vector is a reference signal and the other is an unknown signal.

The measurement error is the error obtained when one vector is a parameter vector and the other vector contains the true parameters of the structure under investigation.

The interpolation error is the error induced in a parameter vector by interpolation. If $r_p$ and $p_p$ are a measurement vector and associated parameter vector in a library, then matching $r_p$ as an unknown signal against that library would return a perfect match with no error. If $r_p$ is deleted from the library before the matching and the match algorithm returns an interpolated estimate of the associated parameters, $p_e$, then $\epsilon(p_p, p_e)$ is the interpolation error.

A reference library is pruned according to the invention by removing the reference vectors for which the interpolation error is less than a threshold value.

A reference library is preferably indexed according to the invention by comparing each reference signal with a basis signal to produce a value, $i_{1r}=f(r,b_1)$, where $b_1$ is a basis vector. Libraries are multiply indexed by calculating an index vector defined as $i_r=(i_{1r}, i_{2r}, \ldots, i_{1r})$, where each index value is calculated as in the single index case. There are many sources of basis vectors and a multiple index scheme uses N indexes using N basis vectors. The Fourier basis set is one possible source of basis vectors, as are the Hadamard, Discrete Cosine, wavelet, or principal components. Note that the wavelet and principal component basis vectors must first be computed from the signals in the reference library. Methods of computing these basis sets are known to those of ordinary skill in the art.

An index vector for an unknown signal, u, is calculated in the same manner as for a reference signal to yield $i_u=(i_{1u}, i_{2u}, \ldots, i_{1u})$.

There are two ways to use the index vectors. In the first method, the error between the unknown signal index vector and each reference signal index vector, $\epsilon(i_u, i_r)$, is calculated, if the error is less than some threshold, then the associated reference signal is identified as a match candidate and processed further.

The second way to use the index vectors is to calculate the absolute difference between the unknown signal index vector and each reference signal index vector $d=|i_u-i_r|=(d_1, d_2, \ldots, d_1)$, and then compare the difference vector to a threshold vector, $t=(t_1, t_2, \ldots, t_1)$. Candidate signals are those for which $d_n<t_n$ for every index.

A brute force search is one in which the error between every reference signal in the candidate set and the unknown signal $\epsilon(u,r)$ is calculated. The reference signal with the smallest error may be returned as the best match or a parameter vector calculated via interpolation of the M closest matches may be returned as the best match.

Even with the most advanced indexing such as that provided by the present invention, library matching is an intensive operation. All of the steps discussed so far are designed to reduce both the number of floating point calculations which must be performed as well as the number of bytes which must be transferred between storage and the computer CPU. Faster matches result from a network reachable computer dedicated to matching unknown signals to reference signals. One reason this is preferred is because the signal matching process is not preempted by other tasks.

The speed with which the match computer transfers data from permanent storage to it's own local random access memory can reach the tens of seconds. Two techniques either reduce or eliminate the transfer time. First, a very large ramdisk, where a file system is mimicked in the computer's random access memory, greatly reduces transfer times. Second, writing the matching program as a server within a client server architecture eliminates the transfer time in many cases. This works because the server program loads a library into memory when a match against that library is requested. The library remains in memory until it is either displaced by another library or the server program terminates. As long as the server program does not terminate, any number of match results may be generated with little effect from transfer time.

Further reductions in match time result from running more than one match server for a library. Given N match servers, a library is divided into N parts, each of which is smaller than the entire library. Each section of the library is matched separately and in parallel with the other sections on the library. The results from matching within each section are then collected and processed to produce the final result. If the single computer match time is t, then in general, the parallel match time with N computers is $$\frac{t}{N} + o,$$

where o is the overhead associated with the parallel algorithm.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all reference, applications, patents, and publications cited above are hereby incorporated by reference.

What is claimed is:

1. A method of pruning a reference library of signatures and corresponding known structure parameter vectors, each signature comprising a reference signal vector, the method comprising the steps of:

generating a library of metrology reference signal vectors;

for at least one given reference signal vector, interpolating a parameter vector assuming that the given reference signal vector and its corresponding parameter vector were deleted from the reference library; and deleting the given reference signal vector and the corresponding parameter vector if an interpolation error between the corresponding parameter vector and the interpolated parameter vector is less than a threshold value.

2. The method of claim 1 additionally comprising the step of repeating the interpolating and deleting steps a predetermined plurality of times for a plurality of given reference signal vectors.

3. The method of claim 1 wherein performance of the steps is submitted to a remote computer on a computer network.

4. The method of claim 3 wherein results of the steps are retrieved from or returned by the remote computer.

5. The method of claim 3 wherein the steps are performed utilizing a dedicated CD-ROM on the remote computer.

6. The method of claim 3 wherein the steps are performed utilizing a dedicated ramdisk on the remote computer.

7. The method of claim 3 wherein performance of the steps is submitted and results retrieved automatically.

8. The method of claim 3 wherein performance of the steps is submitted and results retrieved manually.

9. A method of accessing an indexed reference library of signatures and corresponding known structure parameter vectors, each signature comprising a reference signal vector, the method comprising the steps of:

acquiring an unknown metrology signal;

calculating an index vector for the unknown metrology signal;

calculating a plurality of reference signal index vectors from the reference signal vectors of the library;

determining error between the index vector for the unknown metrology signal and the reference signal index vector; and identifying as a match candidate for the unknown metrology signal a reference signal vector corresponding to the reference signal index vector if the error is below a predetermined threshold.

10. The method of claim 9 additionally comprising the step of establishing a plurality of computer systems for performing the calculating, determining, and identifying steps, wherein each of the computer systems performs the steps on a discrete portion of the reference library.

11. The method of claim 9 additionally comprising the step of performing the calculating, determining, and identifying steps for a plurality of reference signal index vectors.

12. The method of claim 9 wherein performance of the steps is submitted to a remote computer on a computer network.

13. The method of claim 12 wherein results of the steps are retrieved from or returned by the remote computer.

14. The method of claim 12 wherein the steps are performed utilizing a dedicated CD-ROM on the remote computer.

15. The method of claim 12 wherein the steps are performed utilizing a dedicated ramdisk on the remote computer.

16. The method of claim 12 wherein performance of the steps is submitted and results retrieved automatically.

17. The method of claim 12 wherein performance of the steps is submitted and results retrieved manually.

18. A method of accessing an indexed reference library of signatures and corresponding known structure parameter vectors, each signature comprising a reference signal vector, the method comprising the steps of:

acquiring an unknown metrology signal;

calculating an index vector for the unknown metrology signal; calculating a plurality of reference signal index vectors from the reference signal vectors of the library;

determining an absolute difference vector from the index vector for the unknown metrology signal and the reference signal index vector; and identifying as a match candidate for the unknown metrology signal a reference signal vector corresponding to the reference signal index vector if all values in the absolute difference vector are below corresponding values in a predetermined threshold vector.

19. The method of claim 18 additionally comprising the step of establishing a plurality of computer systems for performing the calculating, determining, and identifying steps, wherein each of the computer systems performs the steps on a discrete portion of the reference library.

20. The method of claim 18 additionally comprising the step of performing the calculating, determining, and identifying steps for a plurality of reference signal index vectors.

21. The method of claim 18 wherein performance of the steps is submitted to a remote computer on a computer network.

22. The method of claim 21 wherein results of the steps are retrieved from or returned by the remote computer.

23. The method of claim 21 wherein the steps are performed utilizing a dedicated CD-ROM on the remote computer.

24. The method of claim 21 wherein the steps are performed utilizing a dedicated ramdisk on the remote computer.

25. The method of claim 21 wherein performance of the steps is submitted and results retrieved automatically.

26. The method of claim 21 wherein performance of the steps is submitted and results retrieved manually.

* * * * *